United States Patent
Campbell

(10) Patent No.: US 7,413,306 B2
(45) Date of Patent: Aug. 19, 2008

(54) SPHERO CYLINDRICAL EYE REFRACTION SYSTEM USING FLUID FOCUS ELECTROSTATICALLY VARIABLE LENSES

(75) Inventor: Charles E. Campbell, Berkeley, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 252 days.

(21) Appl. No.: 10/993,409

(22) Filed: Nov. 18, 2004

(65) Prior Publication Data

US 2006/0106426 A1 May 18, 2006

(51) Int. Cl.
*A61B 3/02* (2006.01)
*G02C 7/02* (2006.01)
*G02B 3/12* (2006.01)
*G02B 1/06* (2006.01)

(52) U.S. Cl. .................. 351/233; 351/159; 359/666
(58) Field of Classification Search ......... 359/665–667; 351/228, 159, 176, 233
See application file for complete search history.

(56) References Cited

U.S. PATENT DOCUMENTS

| | | | |
|---|---|---|---|
| 3,751,138 | A | 8/1973 | Humphrey |
| 3,976,364 | A | 8/1976 | Lindemann et al. |
| 4,407,567 | A | 10/1983 | Michelet et al. |
| 4,989,958 | A | 2/1991 | Hamada et al. |
| 5,066,301 | A | 11/1991 | Wiley |
| 6,369,954 | B1 | 4/2002 | Berge et al. |
| 6,449,081 | B1 | 9/2002 | Onuki et al. |
| 6,491,394 | B1 * | 12/2002 | Blum et al. ............. 351/228 |
| 6,545,815 | B2 | 4/2003 | Kroupenkine et al. |
| 6,924,792 | B1 | 8/2005 | Jessop |
| 7,310,080 | B2 | 12/2007 | Jessop |
| 2003/0085850 | A1 | 5/2003 | Feenstra et al. |
| 2005/0185135 | A1 * | 8/2005 | Blum et al. ............. 351/168 |
| 2006/0072070 | A1 | 4/2006 | Kuiper et al. |
| 2006/0079728 | A1 | 4/2006 | Kuiper et al. |
| 2006/0170864 | A1 | 8/2006 | Kuiper et al. |
| 2006/0244902 | A1 * | 11/2006 | Kuiper et al. ........... 351/159 |

FOREIGN PATENT DOCUMENTS

| | | | |
|---|---|---|---|
| JP | 03004211 A * | 1/1991 | |
| WO | WO 03/069380 A1 | 8/2003 | |

(Continued)

OTHER PUBLICATIONS

"About Surface Tension Measuring Instruments" downloaded from <<http://test-equiptment.globalspec.com/...>> (Oct. 28, 2004) 3 pages total.

(Continued)

*Primary Examiner*—Scott J. Sugarman
(74) *Attorney, Agent, or Firm*—Townsend & Townsend & Crew LLP; Mark D. Barrish

(57) ABSTRACT

Optical devices, systems, and methods can produce and/or measure cylindrical (as well as spherical) lens shapes throughout a range of both powers and cylindrical axes. Fluid focus lenses employ electrical potentials to vary the shape of a fluid/fluid interface between two immiscible fluids having differing indices of refractions by controlling localized angles between the interface and a surrounding container wall. Spherical power, cylindrical power, and cylindrical access alignment may be varied with no moving parts (other than the fluids).

14 Claims, 4 Drawing Sheets

FOREIGN PATENT DOCUMENTS

| WO | WO 03/071335 A2 | 8/2003 |
| WO | WO 2004/038480 A1 | 5/2004 |

OTHER PUBLICATIONS

"Stepper Motor System Basics" AMS Advanced Micro Systems, Inc, downloaded from <<file://U/ams2000/stepping101.html>> (Aug. 7, 2000) 9 pages total.

"Industrial Circuits Application Note: Drive Circuit Basics" pp. 1-7.

"Motor Technologies" Parker Motion & Control, pp. A4-A8.

"Philips' Fluid Lenses Bring Things Into Focus" downloaded from <<http://www.research.philips.com...>>(Apr. 9, 2004) 3 pages total.

\* cited by examiner

SPHERO CYLINDRICAL EYE REFRACTION SYSTEM USING FLUID FOCUS ELECTROSTATICALLY VARIABLE LENSES

BACKGROUND OF THE INVENTION

The present invention is generally related to optical devices, systems, and methods, and in one embodiment provides a fluid lens capable of being adjusted in spherical and/or cylindrical power so as to allow, for example, correction of refractive errors of the human eye.

Refractive errors of the human eye are measured in a variety of ways, including both subjective and objective approaches. Subjective measurements of the eye may be made by placing corrective lenses or a corrective optical system before the eye and conducting a controlled test of the resulting corrected vision. These eye tests are commonly used to identify a sphero-cylindrical correction that provides improved vision to a subject while that subject is reviewing a suitable target image.

When conducting subjective refraction measurements, a series of individual trial lenses may be positioned before the eye of the test subject. In many subjective refraction tests, the subject looks through a phoropter, an instrument having a bank of lenses. The lenses of the phoropter can be positioned sequentially in front of the eye, with the subject often choosing between two or more alternative lens arrangements so as to provide the most improved visual acuity. Although some modern phoropters have motorized mechanisms that move or select the lenses, most remain manual devices.

In addition to the subjective measurements of human refractive errors, there are a variety of structures intended to produce objective measurements of the human eye. Objective measurements may be made by a variety of automatic refractors, for example. These instruments often have variable correcting optical trains that can correct either spherical errors alone, or that can correct sphero-cylindrical errors of the eye throughout an adjustment range. Automatic refractors alter the spherical (and often the cylindrical) power of an optical train using motors, gears, slides, bearings, pulleys, and/or the like. These moving components tend to make automatic refractors complex, bulky, susceptible to wear and damage, and quite expensive.

In light of the above, it would be advantageous to provide improved optical devices, systems, and methods. It would be particularly beneficial if these improvements allowed adjustment, correction, and/or measurement of spherical, cylindrical, toroidal, and possibly other errors, particularly for measurement of errors of the human eye. It would be particularly advantageous if these improvements could be realized without relying on a large number of alternative lenses and without the motors, gears, slides, bearings, pulleys, and other moving parts of known eye measurement systems.

BRIEF SUMMARY OF THE INVENTION

The present invention generally provides improved optical devices, systems, and methods. Embodiments of the present invention can produce sphero-cylindrical, cylindrical spherical, and other lens shapes throughout a range of powers and cylindrical axes. The invention often makes use of fluid focus lenses employing electrical potentials to vary the shape of a fluid/fluid interface. The fluid/fluid interface between two immiscible fluids having differing indices of refractions can be altered by varying a position and/or angle of the interface relative to a surrounding container wall. In some embodiments, the container may have the form of a rectangular prism, with a cylindrical lens being formed by applying a potential to opposed side walls of the prism, optionally with a different potential applied to end walls of the prism. Alternative embodiments may make use of a substantially cylindrical container with a series of electrodes distributed circumferentially about an optical path, so as to allow both spherical, cylindrical, and other powers to be varied. Advantageously, no moving parts (other than the fluids) may be employed, even when providing independently variable spherical power, cylindrical power, and cylindrical orientation throughout the full range of human eye vision adjustment.

In a first aspect, the invention provides an optical apparatus comprising at least one housing defining at least one opening having an optical path therethrough. A plurality of fluids are disposed in the at least one opening so as to define one or more fluid/fluid interfaces. An electrical potential source is coupled to the at least one opening. The source is configured to vary at least one electrowetting potential so as to change a cylindrical orientation of the one or more fluid/fluid interfaces in response to a first input.

The source may be configured to alter the at least one electrowetting potential so as to change a cylindrical power in response to a second input, and/or to alter the at least one electrowetting potential so that the one or more fluid/fluid interfaces vary in spherical power in response to a third input. Preferably, the spherical power may be varied throughout a range from at least about minus 20.0 diopters to at least about plus 20.0 diopters so as to accommodate substantially the full range of human eye spherical aberrations. Similarly, the apparatus will preferably have cylindrical powers which can be varied throughout a range from at least minus 6.0 diopters to at least plus 6.0 diopters, with the cylindrical orientation variable throughout a range of ate least about 90°; optionally being at least about 180°, so that the optical apparatus can compensate for substantially the full range of cylindrical aberrations in the human eye.

Optionally, the at least one housing may define a first opening with a first fluid/fluid interface therein and a second opening with a second fluid/fluid interface therein. The first and second openings may each comprise a rectangular cross section relative to the optical path. Varying of a first electrowetting potential may effect changes in a first variable cylindrical power of the first fluid/fluid interface, the first variable cylindrical power having a first cylindrical orientation extending laterally across the optical path. Varying a second electrowetting potential may effect changes in a second variable cylindrical power of the second fluid/fluid interface, the second variable cylindrical power having a second cylindrical orientation extending laterally across the optical path. The first cylindrical orientation may be angularly offset from the second cylindrical orientation about the optical path.

The at least one housing may define a third opening with a third fluid/fluid interface therein, the third opening comprising a rectangular cross section. Varying of a third electrowetting potential may effect changes in a third variable cylindrical power of the third fluid/fluid interface disposed within the third opening. The third variable cylindrical power has a third cylindrical orientation extending laterally across the optical path, the third cylindrical orientation being angularly offset from the first and second cylindrical axes about the optical path. For example, the first cylindrical orientation may be substantially perpendicular to the second cylindrical orientation, while the third cylindrical orientation is angularly offset from the first cylindrical orientation by about 45°.

In many embodiments, first and second electrodes may be disposed along opposing sides of the first opening. Similarly, third and fourth electrodes may be disposed along opposing sides of the second opening, while fifth and sixth electrodes are disposed along opposing sides of the third opening. The electrodes along opposing sides of each opening may be coupled electrically so that a common electrowetting potential can be easily applied to both sides of each opening. Varying the electrowetting potential along both sides of the opening can controllably vary angles defined between the sides of the rectangular opening and the fluid/fluid interface within that opening, and/or vary positions of the fluid/fluid interface along the container wall adjacent the potential. This can be used to variably control the cylindrical power of the fluid/fluid interface, particularly where ends of the rectangular opening (connecting the opposed sides) are configured to maintain a 90° angle between the fluid/fluid interface and the end surface, such as by providing an end electrode at an appropriate electrowetting potential for each end of each rectangular opening.

In some embodiments, the housing may comprise a wall disposed around the optical path, and may further include a plurality of conductors distributed circumferentially about the wall. The conductors may define an electrode array, with each electrode of the array disposed circumferentially between (and electrically separated from) two adjacent electrodes of the array. There will often be five or more electrodes in this circumferential array, optionally being eight or more electrodes, and in some embodiments being ten or more electrodes. The power source may apply a circumferential series of potentials about the optical path. The series of potentials may comprise a substantially sinusoidal pattern of DC voltages. The power source may be configured to vary an amplitude of the sinusoidal pattern in response to the second input. The power source may also be configured to rotate the sinusoidal voltage pattern about the optical path in response to the first input. Preferably, the power source is configured to vary an average voltage of the pattern in response to a third input so as to alter a spherical power along the optical path.

In many embodiments, the optical apparatus may vary the cylindrical power and the cylindrical orientation by affecting movement of the fluids within the at least one housing and without affecting other movement of the apparatus. The power source may comprise a processor, with the processor determining a plurality of electrowetting potentials in response to the first and second inputs. The processor may further determine the electrowetting potentials in response to a third input so as to vary a spherical optical power along the optical path. The at least one fluid/fluid interface may optionally be capable of acting as a pure cylindrical lens without significant spherical power along the optical path.

In another aspect, the invention provides a fluid cylindrical lens apparatus comprising a first housing having a first prismatic opening with an optical path therethrough. The first opening has a first surface and a second surface, the second surface being offset from the first surface with an optical path therebetween. A plurality of fluids are disposed in the opening so as to define a first fluid/fluid interface traversing the first and second surfaces. An electrical potential source is coupled to the first and second surfaces to apply a first variable potential thereto so as to change a first variable cylindrical power of the fluid/fluid interface along the optical path.

The first variable cylindrical power will often have a first orientation that traverses end surfaces of the first opening. The potential source may apply another potential to the end surfaces, with the other potential being different than the first potential, particularly when the first cylindrical power is different than zero. The fluid cylindrical lens apparatus may also include a second housing having a second opening with a third surface and a fourth surface with the optical path therebetween. A plurality of fluids may be disposed in the second opening so as to define a second fluid/fluid interface. The power source may be coupled to the third and fourth surfaces so as to apply a second variable potential thereto that changes the second variable cylindrical power. The second variable cylindrical power may have a second orientation which is angularly offset about the optical path relative to the first orientation. A third housing may have a third opening. The third opening may have fifth and sixth surfaces with the optical path again therebetween. Once again, a plurality of fluids may be disposed in the third opening so as to define a third fluid/fluid interface. The potential source may be coupled to the fifth and sixth surfaces to apply a third variable potential so as to change a third cylindrical power having a third orientation. The third orientation may be angularly offset from the first and second axes, thereby allowing the apparatus to vary spherical power along the optical path, cylindrical power along the optical path, and cylindrical orientation about the optical path.

In yet another embodiments, the invention provides an optical apparatus comprising at least one housing defining at least one opening having an optical path extending axially therethrough. A plurality of fluids are disposed in the at least one opening so as to define at least one fluid/fluid interface. A plurality of electrical conductors are distributed circumferentially about the optical path. An electrical potential source is coupled to the electrical conductors so as to simultaneously apply a plurality of differing electrowetting potentials thereto. The source is configured to alter the at least one fluid/fluid interface so as to controllably vary at least a sphero-cylindrical power along the optical path.

Optionally, the housing may comprise a substantially cylindrical wall, prismatic, or other shaped wall extending around the optical path. The electrical conductors may be distributed circumferentially about the wall. There will often be four or more electrical conductors, often being five or more electrical conductors, and in many cases, eight or more electrical conductors distributed circumferentially about the wall. The source may be configured to alter the fluid/fluid interface so as to vary a spherical power along the optical path, and optionally, a cylindrical orientation of the cylindrical power. Each electrical conductor may extend along the optical path, and a spherical power along the optical path may be varied by varying the average potential applied to the electrical conductors. In addition to providing cylindrical and spherical powers, such a structure may also provide other anamorphic lens shapes. The potentials may differ circumferentially, and some embodiments may employ a plurality of openings, each having a fluid/fluid interface, so that not all of the differing potentials need be applied about the same opening.

In yet another aspect, the invention provides a phoropter or automatic refractor comprising at least one housing defining at least one opening having an optical path therethrough. A plurality of fluids are disposed in the at least one opening so as to define one or more fluid/fluid interfaces. A plurality of electrical conductors are disposed near the at least one opening, and an electrical potential source is coupled to the electrical conductors so as to apply at least one electrowetting potential. The source is configured to alter the one or more fluid/fluid interfaces so as to controllably vary one or more characteristics selected from among: a spherical power along the optical path; a cylindrical power along the optical path; and a cylindrical orientation along the optical path. In many embodiments, the electrical potential source will be configured to alter two or more of the characteristics, in many cases all three of the characteristics.

In yet another aspect, the invention provides a fluid lens optical method comprising configuring one or more fluid/fluid interfaces by applying at least one electrowetting potential so as to change a cylindrical orientation along an optical path.

In many embodiments, the one or more fluid/fluid interfaces is reconfigured by changing the at least one potential so that a cylindrical power can also be changed. A spherical power along the optical axis may also be provided by changing the at least one potential. The cylindrical power, cylindrical orientation, and spherical power may be controllably varied by moving fluids in response to the at least one potential, and without other movement along the optical path.

In yet another aspect, the invention may provide a fluid lens optical method comprising configuring at least one fluid/fluid interface traversed by an optical path by simultaneously applying a plurality of circumferentially differing electrowetting potentials about the optical path. The potentials may be applied so as to simultaneously provide a first curvature of the at least one fluid/fluid interface and a second curvature of the at least one fluid/fluid interface. This may optionally provide a variable sphero-cylinder lens using a single fluid/fluid interface, or using a plurality of fluid/fluid interfaces.

In yet another aspect, the invention provides an optical apparatus comprising at least one housing defining at least one opening having an optical path therethrough. A plurality of fluids are disposed in the at least one opening so as to define at least one fluid/fluid interface. An electrical potential source coupled to the at least one opening is configured to simultaneously apply a plurality of electrowetting potentials so that the at least one fluid/fluid interface controllably varies in spherical and cylindrical power.

DETAILED DESCRIPTION OF THE INVENTION

Figure 1:
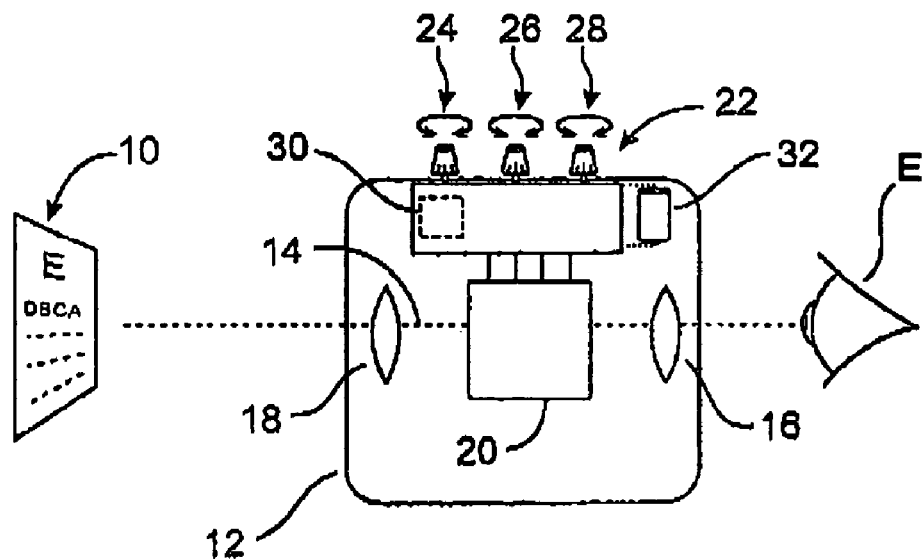
FIG. 1 schematically illustrates an optical apparatus having one or more fluid lenses so as to vary spherical power, cylindrical power, and cylindrical orientation along an optical path, and a method for use of the apparatus for measuring aberrations of a human eye.

The present invention generally provides improved optical devices, systems, and methods. The invention often makes use of fluid lenses, particularly for varying a cylindrical axis or orientation, cylindrical power, spherical power, spherocylindrical characteristics, and/or other optical properties of a fluid/fluid interface. The relatively low cost, small size, light weight, and ease of manufacture of the fluid lenses described herein may allow common optical devices (such as binoculars, telescopes, cameras, microscopes, endoscopes, and even eye glasses) to compensate for cylindrical and/or spherical error of a user's eye by including these fluid lenses therein. While the devices and methods of the present invention are particularly well suited for measuring and/or compensating for standard aberrations of the human eye, they may also find applications in optical recording techniques, optical communications, optical signal processing and telecommunications, digital cameras, camera phones, endoscopes, light and image projection, and the like.

Fluid lenses may comprise two immiscible fluids of differing refractive index. One fluid, for example, may be an electrically conducting aqueous solution, while the other may comprise an electrically non-conducting oil. The fluid lenses may be contained in one or more housings, with internal surfaces of the housing being coated with a hydrophobic coating. In general terms, the molecules of a liquid attract each other. An equal attractive force in all directions balances the interactions of a molecule in the bulk of each liquid, while the molecules on the surfaces of the liquid experience an imbalance of forces, resulting in the presence of energy at the interfaces. This energy generates an interface tension. Hydrophobic coatings may increase the interface tension of at least one of the fluids, for example, changing a contact angle between the fluid/fluid boundary and the hydrophobic coating. This interface tension can also limit contact between the hydrophobic coating and the aqueous solution, causing the aqueous solution to form itself into a mass along one end of the container and the fluid/fluid interface to curve in a controllable manner. Hence, this curving fluid/fluid interface may act as a lens along an optical path traversing the interface.

The shape of the fluid/fluid interface of a fluid lens may be adjusted by applying one or more electrical fields across the hydrophobic coating such that it becomes less hydrophobic. This process is sometimes referred to as "electrowetting" and may electrically induce changes in the static contact angle between the fluid/fluid interface and the adjacent surface of the container wall. By altering the boundary conditions of the fluid/fluid interface along the wall, the electrical potential can drive the interface to a different boundary configuration, and also to a new overall shape with desired refractive properties throughout the fluid/fluid interface. These changes in the interface shape may be induced by changing the static contact angle between a solid container wall and the fluid/fluid boundary, which may in turn be induced by altering the relative interface tensions. Once the boundary conditions are set by appropriate electrowetting potential(s) along the container walls, the rest of the surface may assume a shape to minimize the surface energy associated with the interface tension, or to minimize surface area of the interface.

Embodiments of the invention may control the refractive properties of fluid lenses by locally varying the boundary conditions of the fluid/fluid interface about a perimeter of the fluid/fluid interface. The boundary conditions, and specifically the static contact angle of the fluid/fluid interface against the container wall, may optionally be determined using a wetting coefficient K, where K=cos α (α being the static contact angle between the fluid/fluid boundary and the container wall) as follows:

$$K = \frac{\sigma_{sfp} - \sigma_{sfn}}{\sigma_{ff}}$$

in which $\sigma_{ff}$ is the interface tension between the two fluids, $\sigma_{sfp}$ is the interface tension between the more polar of the two fluids and the solid container wall, and σsfn is the interface tension between the non-polar fluid and the solid container wall. Liquids (such as water) having relatively strong intermolecular interactions (and thus high interface tensions) are referred to as polar liquids, while liquids having lower surface tensions are referred to as non-polar. The immiscible liquids A and B in the fluid lenses described herein will often include one relatively polar fluid and one relatively non-polar fluid, which is less polar than the polar fluid.

When the electrical field between the surface of the container and the immiscible fluids changes, the interface tension between the solid container wall and the polar fluid may change significantly. The same change in electrical field may induce less change (or even no change or a change in the opposite direction) in the interface tension between the solid container wall and the non-polar fluid. This difference may, at least in part, be related to the imbalance of force on the surface molecules. The polar liquid interface molecules generally induce greater forces when surrounded by similar molecules on one side and something different on the other side. By changing the electrostatic field, the relatively strong attraction of these surface molecules to the polar fluid can be changed, thereby changing the magnitude of the interface tension. The non-polar molecules along the container wall will be effected less by the same change in electrostatic field, so that the interface tension of the non-polar fluid doesn't change as much. As can be seen in the above equation, the numerator of the equation (and hence the wetting coefficient) can undergo a change in magnitude or even sign if one interface tension changes while the other does not (or changes less, or even in an opposite direction). It should be noted, however, that embodiments of the invention need not be tied to a particular theory of operation, and that alternate methodologies may be used to determine the relationship between the applied electrical potential, the fluid characteristics, and the optical properties of the lens, including empirical approaches.

As a result of the change in electrical potential (and hence in static contact angle) and the constrained quantities of fluids and space in the container, the aqueous solution may (for example) increasingly wet the walls of the fluid lens container, altering the location of the fluid/fluid boundary along the container walls as well as the radius of curvature of the fluid/fluid interface (and hence the power of the lens). By increasing an applied electrical field the fluid/fluid interface of the fluid lens can be controllably varied from convex, through completely flat or plano, to concave. The fluid lenses described herein typically will (though they need not necessarily) change from positive to negative power as the interface curvature varies from concave to convex. However, by adding a biasing spherical lens of fixed power, the center of the refracting range may be set at will to any chosen value.

As more fully described in PCT publication WO 03/069380, the full disclosure of which is incorporated herein by reference, one of the two non-immiscible liquids in a fluid lens may comprise an electrically insulating liquid such as silicone oil or an alkane. The electrically conducting liquid may comprise water containing a salt solution. The two liquids preferably have a sufficiently equal density so that the lens functions independently of orientation and without significant gravitational effects between the two liquids. Typical refractive indices of the insulating fluid may be between about 1.25 and 1.60. Typical indices of refraction of the conductive solution may vary from about 1.33 to about 1.48. In many embodiments, an electrical conductor or electrode will be in fluid contact with the conductive fluid within the container of the fluid lens.

The fluid lenses will often be disposed in containers having cross-sectional dimensions (relative to the optical path) of less than about 1 cm, often being less than about 5 mm. Lengths along the optical path for each container may also be less than about 1 cm, often being less than about 5 mm.

Referring now to FIG. 1, a patient views a test image 10 with an eye E through an optical apparatus 12. Eye E will often have at least some spherical error, such as myopia or hyperopia. Eye E may also have a significant regular cylindrical astigmatism. Such astigmatism may fall anywhere throughout a range from hyperopic to myopic, and the axial orientation of that astigmatism may vary. In addition to these regular refractive errors of eye E, the eye may also have significant irregular astigmatism.

Apparatus 12 generally has an optical path 14 providing optical coupling between eye E and test image 10. In addition to ocular optics 16, objective optics 18, and other optional optical components such as apertures and the like, apparatus 12 includes a fluid lens assembly 20 that provides variable spherical and/or cylindrical focus capabilities so as to compensate for the regular astigmatism aberrations of eye E. An eye refractor or other device having such a variable focus sphero cylindrical correction system is often used with a relaying lens system where the action of the sphero cylindrical corrector is relayed into the plane of the pupil of the eye of the subject.

The configuration of at least one fluid/fluid interface is varied by altering an electrowetting potential applied to the fluid lens assembly 20 from a potential source 22. More specifically, source 22 is configured to provide a plurality of electrical potentials which vary in response to a spherical power input 24, a cylindrical power input 26, and a cylindrical orientation input 28. In response to these inputs the processor 30 of source 22 configures the electrowetting potentials so as to generate an overall desired spherical power, cylindrical power, and cylindrical orientation within fluid lens assembly 20 and/or apparatus 12 so as to compensate for the refractive errors.

In some embodiments, the only movable elements along optical path 14 of apparatus 12 are the fluids within the fluid lenses of fluid lens assembly 20. In other embodiments, at least a portion of the defocus and/or astigmatism of eye E may be compensated for using one or more selectable lenses, movement of one or more lenses, and the like. For example, a relatively simply spherical fluid lens such as the FluidFocus™ fluid lens developed by Royal Philips Electronics of the Netherlands might be combined with a Stokes cross cylinder lens assembly so as to provide a full variable focus spherocylindrical corrector. While relying on the fluid lens to provide adjustability for spherical power may provide some advantages over prior phoropters and/or automatic refractors, the complexity, cost, and bulkiness of the mechanical Stokes cross-cylinder lens assembly (or another mechanically adjustable lens system) may remain.

Fluid lens assembly 20 may have a total length along optical axis 14 of 2 cm or less, in some cases having a length of 1 cm or less. The cross sectional dimensions of fluid lens assembly may be 2 cm or less, in many cases being 1 cm or less. Fluid lens assembly 20 may provide spherical powers from +20.0 D to −20.0 D. Spherical and cylindrical powers may be adjustable in increments (for example, in 0.25 D steps) or may alternatively be smoothly and continuously adjustable throughout at least a portion of the overall power range. The cylindrical power input 26 may allow cylindrical powers to be adjusted throughout at least a range from about −6.0 D to +6.0 D, while the cylindrical orientation input 28 allows rotation of the cylindrical axis or orientation about optical path 14 throughout a range of at least about 90°, optionally throughout the range of at least about 180°. Focal ranges provided by fluid lens assembly 20 may extend, for example, throughout a range from about 5 cm to infinity and may be quite fast, with switching of the fluid lenses over the full focal range being complete in less than 100 ms, optionally be complete in less than 10 ms.

Advantageously, fluid lens electrowetting potentials may be provided by a DC voltage source, and may represent primarily a capacitive load, so that the lens assembly lens consumes very little power. Hence, electrical power may optionally be provided by a battery 32 of power source 22. Optical apparatus 12 may thus comprise a portable structure which can be hand moved and/or hand held during use. The durability of fluid lenses can also be quite high, optionally providing over one million focusing operations without loss of optical performance. Fluid lens assembly 20 and apparatus 12 can be both shock resistant and capable of operating over a wide temperature range, making them particularly suitable for mobile applications. Advantageously, high volume manufacturing techniques can be applied for some or all of the components of the fluid lens assembly 20 and apparatus 12.

A first fluid lens component capable of generating a variable power cylindrical lens for use in fluid lens assembly 20 can be understood with reference to FIGS. 2, 3, and 4A-C. First referring to FIG. 2, a housing 40 includes walls forming an opening 42, with the exemplary opening having the form of a rectangular prism. An optical path 44 extends through housing 40 and opening 42, so that materials defining surfaces 46, 48 traversed by the optical path will allow light to pass therethrough.

First and second opposed parallel surfaces 50, 52 of container 42 are offset from optical path 44 with the optical path extending along and between these surfaces. Parallel surfaces 50, 52 are sometimes referred to as "sides" of container 42. End surfaces 54, 56 extend between the side surfaces 50, 52, with the exemplary ends being normal to the sides. While the sides will often be longer than the ends, the ends may also be the same length as the sides or longer than the sides.

Four electrodes 58a, 58b, 58c, and 58d (collectively referred to as "electrodes 58") surround optical path 44, with each of the electrodes extending along an associated side 50, 52, or end 54, 56. Each electrode 58 maintains a substantially uniform electrical field throughout much of, preferably most of, the associated side or end, and is electrically isolated from the circumferentially adjacent electrodes relative to optical path 44. Preferably, side electrodes 58a, 58b are electrically coupled to each other by a conductive structure so that the electrodes are at substantially the same electrical potential. Similarly, end electrodes 58c, 58d may also be coupled so as to be at the same potential. One of surfaces 46, 48 may be coupled to side electrodes 58a, 58b. Hence, the two parallel sides of the container and the "top" (which may be at any orientation) of the container may have an electrical potential field which is applied and/or varied as desired. In some embodiments, the field on the end electrodes 58c, 58d may be kept at a constant strength.

Figure 2:
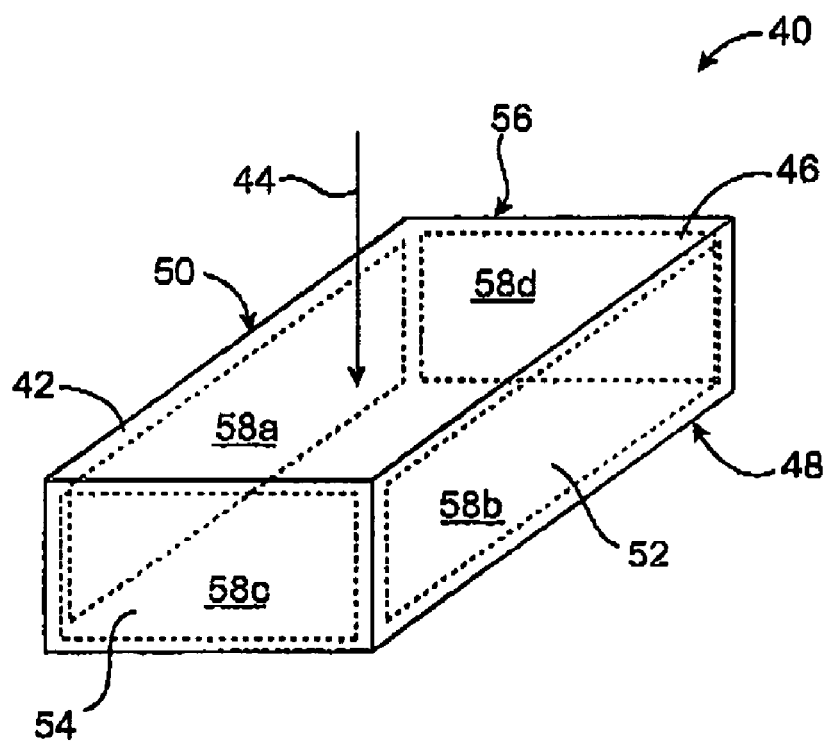
FIG. 2 is a simplified schematic diagram illustrating an arrangement of electrodes about a rectangular opening so as to controllably vary a cylindrical power of a fluid lens within the opening.
Figure 3:
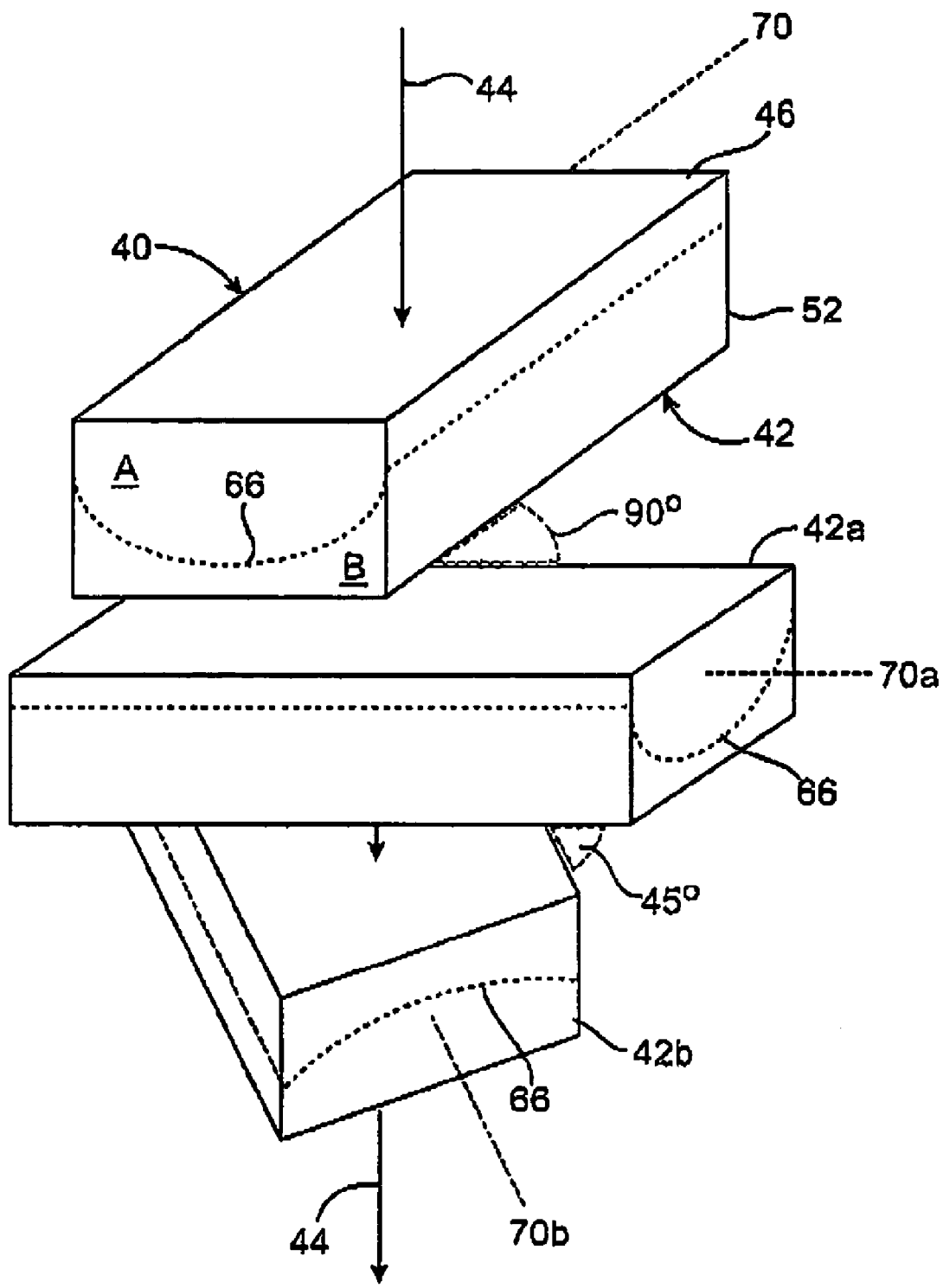
FIG. 3 schematically illustrates three controllably variable cylindrical lenses with axes at differing orientations relative to an optical path so as to allow variations in cylindrical power, spherical power, and cylindrical orientation or axis relative to the optical path.
Figure 4A:
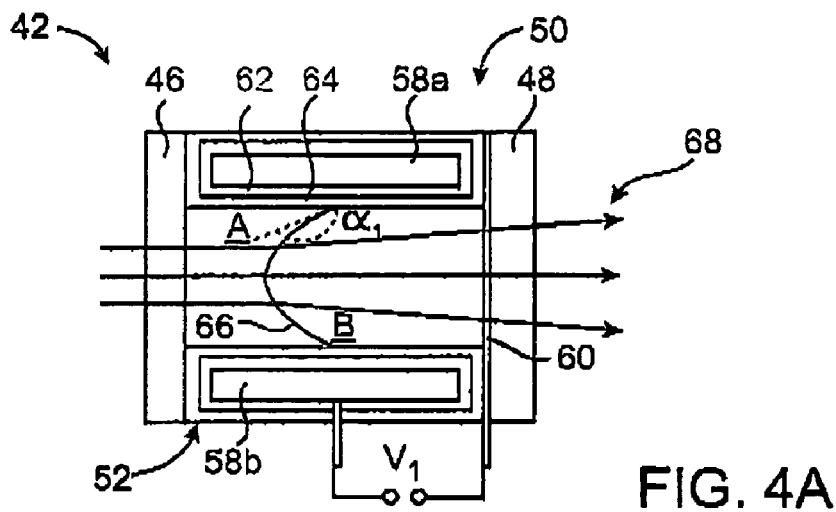
FIGS. 4A through C are cross-sectional views taken through the rectangular fluid lens of FIG. 2 showing some of the internal components, and illustrating how varying of the electrowetting potentials can alter cylindrical power.

As can be understood by reference to FIGS. 2, 3, and 4A, container 42 may contain a non-conductive liquid A and a conductive liquid B which are immiscible and which have differing indices of refraction, as described above. A voltage $V_1$ is applied to side electrodes 58a, 58b relative to an electrode 60 in fluid contact with conductive fluid B. An insulating layer 62 coats side electrodes 58a, 58b, and is in turn coated with a fluid contact layer 64. By applying an appropriate voltage $V_1$ as illustrated in FIG. 4A, a meniscus or fluid/fluid interface 66 between fluids A and B defines a first contact angle $\alpha_1$ at sides 50, 52. As described above, angle $\alpha_1$ may in turn drive the fluid/fluid interface 66 to an appropriately curved configuration so that along the peripheral boundary of interface 66 the tangent to the interface surface shape is at angle $\alpha_1$. Due to the high refractive index of first fluid A relative to second fluid B, the lens formed by fluid/fluid interface 66 has a negative power, as illustrated by the divergent rays 68 traveling along the optical path.

While imposing voltage $V_1$ along sides 50, 52 via electrodes 58a and 58b, a different voltage $V_2$ is also applied to end electrodes 58c, 58d. Under the influence of $V_2$, fluid/fluid interface 66 forms a right angle at ends 54, 56, forcing the cross section between these surfaces to a flat configuration so that the fluid/fluid interface 66 forms a cylindrical lens of variable power, as can be seen in the perspective view of FIG. 3 and the cross-sectional view of FIG. 4B. This second voltage is typically the voltage that would produce a zero power lens were it applied to all four electrodes 58a, 58b, 58c, and 58d.

Figure 4B:
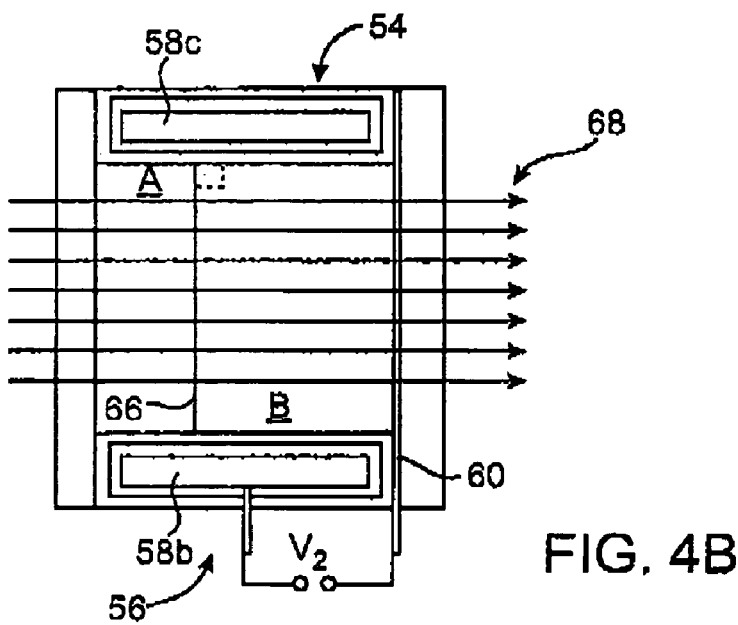
Figure 4C:
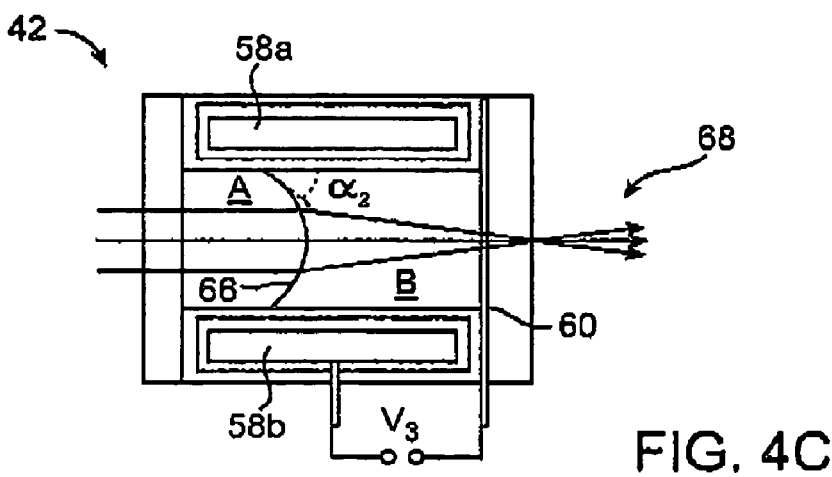

Referring now to FIG. 4C, by applying yet another different voltage $V_3$ to side electrodes 58a, 58b fluid/fluid interface 66 can be driven to a different configuration such that an angle $\alpha_2$ between fluid/fluid interface 66 and the side of container 42 is less than 90°, and the fluid/fluid interface forms a positive lens. In the meantime, voltage $V_2$ (or any appropriate voltage) can still be applied to end electrodes 58c, 58d as shown in FIG. 4B, so that the fluid/fluid interface remains in a cylindrical lens configuration. As the voltage applied to the side electrodes can be continuously varied, the shape of the fluid/fluid interface (and the power of the fluid cylindrical lens) can be smoothly and continuously varied. Along with concave and convex fluid/fluid interface shapes, the fluid lens can also assume a plano or flat configuration.

The shape of the fluid/fluid interface within the lens will generally be driven by the position and/or angle of the lens along the sides and end of the container. Some distortion of an ideal lens shape may occur at the corners between the sides and end, where the electrical fields along the container/fluid interface are defined by some combination of the side and end electrodes. Adjustment to the end electrode voltage can also be made as desired to provide the desired lens properties.

Materials for fabricating container 42 may be similar to those used for spherical fluid lens structures. For example, electrodes 58 and 60 will often comprise a metallic material, while insulating layer 62 may comprise a polymer such as parylene. Fluid contact layer 64 may comprise a fluorocarbon such as a PTFE including Teflon™ produced by DuPont. The transparent surfaces 46, 48 traversed by the optical path may comprise clear polymers, glass, or the like.

Referring now to FIG. 3, a series of rectangular containers 42, 42a, 42b are aligned along optical path 44 so as to allow the cylindrical fluid lenses to generate any desired spherical or cylindrical power, with the cylindrical power being at any desired axial orientation. Container 42 in the fluid lens defined by the fluid/fluid interface therein has a cylindrical axis or orientation 70 extending across optical path 44. A second container 42a and associated fluid cylindrical lens have a second orientation 70a extending across optical path 44, with the second orientation 70a offset from the first orientation 70 by about 90°, as illustrated. A third container 42b has a third orientation 70b which is again offset from the first orientation 70 and from the second orientation 70a, ideally by about 45°.

To understand how three variable power cylinder lenses may be used to create any sphero cylindrical power, the power of a single cylinder lens will first be expressed in terms of the cross-cylinder lens and a sphere lens. A pure cylinder lens of power equal to C has one principal meridional power equal to C and the other equal to O. Its orientation is expressed in terms of its axis, a direction aligned along the meridian of 0 power. But such a lens may also be described in terms of the combination of the pure spherical lens of power C/2 and a cross-cylinder lens of power C/2. A cross-cylinder is defined as the combination of two pure cylinder lenses of equal but opposite power C/2 oriented with respect to one another such that their axes are at right angles. The orientation of this cross cylinder is defined as the orientation of the axis of one of the pure cylinder lenses that make the cross-cylinder.

This decomposition method for describing a pure cylindrical power in terms of a sphere and cross-cylinder is now extended to any sphero cylindrical combination which is typically expressed in terms of a sphere power, a cylinder power and an orientation. The concept of the sphere equivalent can then be introduced. Sphere equivalent is the sphere power of the sphero cylindrical combination plus one half the cylinder power. Sphere equivalent can thus take the place of the sphere component described above for the pure cylinder lens. The cross-cylinder component power is again one half the cylinder power. Indeed, the pure cylinder is just a sphero cylindrical combination with the sphere equal to zero.

When expressed in this fashion, sphero cylindrical powers form a 3 dimensional vector space with one axis the sphere equivalent value and the other two axes forming a cross-cylinder double angle vector space.

Now considering a desired sphero cylindrical power with values sphere=S, cylinder=C and axis or orientation=A, in this type of representation of sphero cylindrical power the sphere may take a positive or negative value but the cylinder always has the same sign. Let us use a positive cylinder value for easy of exposition. This may be expressed in terms of the three refractive space components Sphere equivalent ($SE$)=$S/2$ Cross-cylinder at 0-90° ($C+$)=$C/2 \cos(2A)$ Cross-cylinder at 45-135° ($Cx$)=$C/2 \sin(2A)$ In the double angle cross-cylinder space, the C+ axis is at right angles to the Cx axis so in this space, the two cross-cylinder components form a true vector. If cross-cylinder components, unlike the cylinder value, can take positive or negative values and if the sign of a component is changed, it flips through 180° in the double angle cross-cylinder space. Let us orient that fluid focus cylinders so that one has its axis at 0°, one has its axis at 90° and the other has its axis at 45°. If then the same power is created in the cylinder at 0° and the one at 90°, their sphere equivalent components will be equal. Their cross-cylinder components will both be only of the C+ variety and will have equal magnitudes but they will have opposite signs because they are oriented at 90° from one another. This means when they are added as vectors in the double angle cross-cylinder space, they will cancel one another and the result will be only the addition of the two sphere equivalent components giving a net result of a spherical lens effect. The effect of creating a spherical effect with two pure cylinders show how this theory gives expected results.

The other variable cylinder can only create a Cx component, i.e. one oriented at 45 or 135° depending on whether the variable cylinder is given a positive or negative power. This is the only variable power lens that can create Cx, it will be treated first. Knowing the desired value of Cx from the decomposition of the desired sphero cylindrical combination, the power of the variable cylinder is increased until it creates with cross cylinder power. If the power of this variable cylinder lens be designated C45, then $$C_{45}=2Cx \quad (1)$$

At the same time it creates a sphere equivalent power $SEcx=C45/2=Cx$. This value mayor may not have the right sign to partially supply the needed SE but it is now subtracted from that value to see how much more SE value is needed. This will be called $SE'=SE-Cx$. This value should now be supplied by the other two variable cylinder lenses in addition to supplying the needed C+ component.

Let us define the cylinder power of the variable cylinder with axis 0 degrees as Co, and the cylinder power of variable cylinder with axis 90 degrees as C90. Both these power may be positive or negative. The sphere equivalent power of the Co is Co/2 and the sphere equivalent power of the C90 is C90/2. Their sum should equal SE' so:

$$SE-Cx=Co/2+C90/2$$

Likewise the sum of the cross-cylinders created by these two variable focus lenses equals the value C+. However the sign of the cross-cylinder created by the C90 variable power lens can have its sign changed for the reasons explained above so:

$$C+=Co/2-C9012$$

These two equations may now be solved for the values Co and C90 by adding them to find Co and then subtracting them to find C90. This results in the expressions of:

$$SE-Cx+C+=Co$$

$$SE-Cx-C+=C90$$

By independently driving the fluid/fluid interfaces of the three containers 42, 42a, 42b to appropriate positive or negative configurations using an electropotential source, the combination of these three fluid lenses can reproduce any desired spherical power, cylindrical power, and cylindrical orientation. Hence, processor 30 of source 22 (see FIG. 1) can identify appropriate configurations for the three fluid lenses so as to generate the combined optical properties indicated at inputs 24, 26, 28. Advantageously, these optical properties can be provided and varied by appropriate application of electrowetting potentials to containers 42, 42a, and 42b, without mechanical movement of optical structures (other than the movement of fluids within the containers). While containers 42, 42a, and 42b will often comprise separate structures each defined by its own housing 40, alternative embodiments may make use of an integral housing to define the three separate containers. It may also be possible to allow fluid communication between the openings. A variety of refinements may also be made, such as providing elongate openings with ends of the openings being significantly separated from optical path 44 so that distortion at the corners or ends has less effect.

In some embodiments, the ends may simply be grounded, and a variety of other refinements may also be employed.

The above includes descriptions of fluid lenses having prismatic containers, and in which electrowetting potentials applied to opposing surfaces of the containers can by varied so as to provide varying cylindrical powers of a fluid/fluid interface bordered by the opposing surfaces. More generally, by varying an electrowetting potential circumferentially about the periphery of a fluid/fluid interface, a desired shape can be generated throughout the fluid/fluid interface. The control over the shape of the fluid/fluid interface from its periphery is (in some ways) analogous to controlling the shape of a bubble.

In the case of a bubble, the shape of the boundary can force the fluid film to take a very specific shape. The boundary of a bubble can be described as having an elevation above some base plane. In the case of the fluid/fluid boundary it may be the first derivative or surface slope that is set at the boundary, not the elevation. Regardless, once the boundary (elevation or slope) is set (for example, by setting a circumferentially local electrowetting potential), the overall surface can be forced to take a very definite shape, particularly once the additional constraint of the interface tension is introduced. The fluid/fluid interface tension will generally cause the interface surface to change shape until the mean curvature is equal everywhere. Until this occurs, the interface tension will create a pressure gradient and fluid will flow.

Spherical surfaces have the property that curvature is equal throughout the surface. Sphero cylindrical or toroidal surfaces have the property that mean curvature can be equal throughout the surface. This can occur because the astigmatic portion can be considered to have zero mean curvature and the spherical equivalent portion has the same curvature—non-zero usually—everywhere. Therefore, sphero cylindrical surfaces will have the advantageous property that they can exist in equilibrium within a fluid/fluid interface. As these shapes can be determined from their boundary conditions, a peripheral electrowetting potential may be used to set the specific sphero-cylinder that will form.

In addition to spheres, toroids, and sphero-cylinders, the structures, methods, and systems described herein may also provide other surfaces that can be described as the combination of a sphere (having constant curvature) and any other shape with a zero mean curvature (in other words, in which the Laplacian is equal to zero). Along with combinations of spheres and cylinders, other shapes such as a trefoil or quadrafoil (which have a zero Laplacian) may also be combined with spheres and/or cylinders, or with each other.

Figure 5:
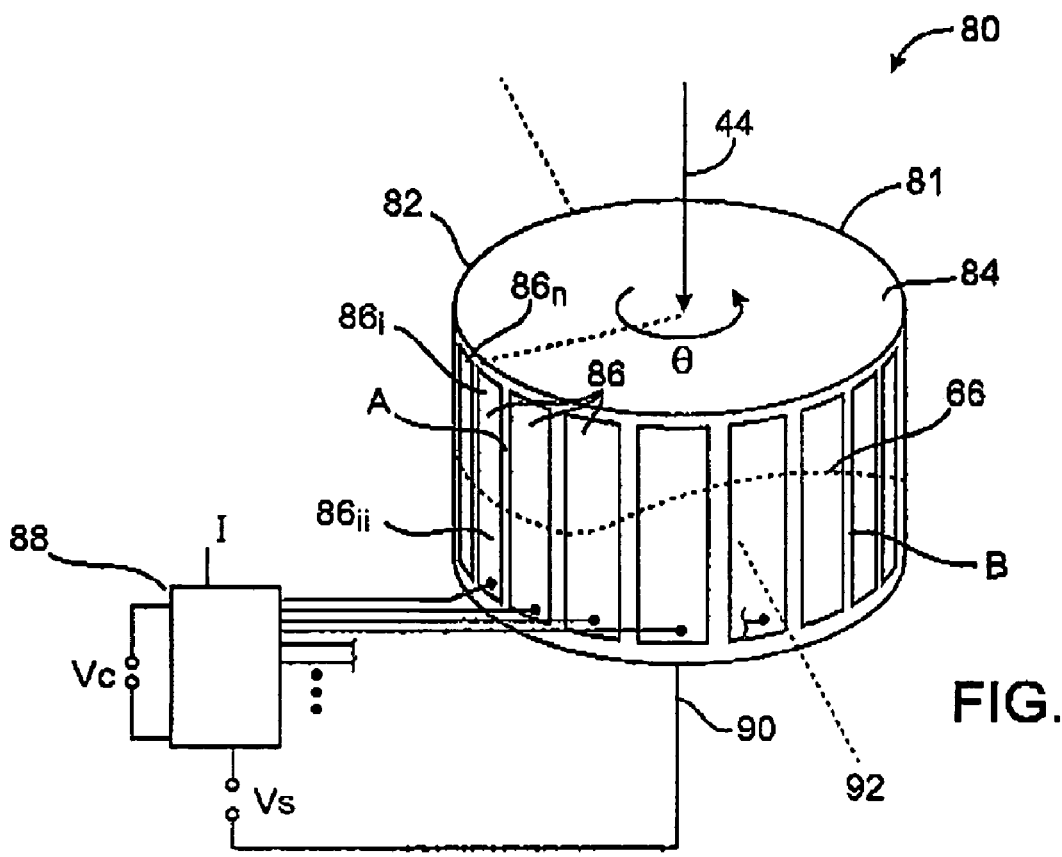
FIG. 5 schematically illustrates an alternative fluid lens having a substantially cylindrical electrode array distributed circumferentially about an optical axis so as to vary a single fluid/fluid interface to provide spherical power, cylindrical power, and cylindrical orientation or axis throughout a range of differing conditions.

Referring now to FIG. 5, a highly flexible spherical/cylindrical (or other shape) fluid lens 80 comprises a housing defining a container 81 with a substantially cylindrical wall 82 surrounding optical path 44. Transparent caps 84 contain first and second fluids A, B within wall 82 and a circumferential series of electrodes 86 are disposed about the wall. A power source 88 is coupled to each electrode 86 of the array so as to apply a variable electrical potential to that electrode.

The potentials may be varied across the array so that a potential at a given electrode of the array may be different than the potentials of both circumferentially adjacent electrodes. The electrodes may be coated with insulating and/or hydrophobic materials as described above, so that electrowetting potentials applied at each electrode 86 of the array, relative to a cap electrode 90 help determine a contact angle of fluid/fluid interface 66 along that electrode, as well as a position of the fluid/fluid interface along the electrode (once the interface has assumed its stable, low energy configuration).

Figure 7A:
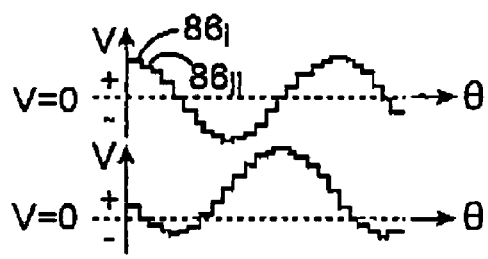
FIGS. 7A and 7B graphically illustrate varying electrical potentials applied to the circumferential electrode array of the fluid lens apparatus of FIG. 5 so as to vary spherical power, cylindrical power, and cylindrical axial alignment.

Referring now to FIGS. 5 and 7A, source 88 may apply a sinusoidal pattern of electrical potentials to electrodes 86 of the array. The sinusoidal pattern defines a stepped series of voltages about the array beginning at a first electrode 86$i$, with a slight variation to the next electrode 86$ii$, and so on to a final voltage at 86$n$. The sinusoidal pattern may define a complete $2\pi$ sine wave about the circumference $\theta$ of container 82. This may drive the contact angle formed between interface 66 and wall 82 to a substantially corresponding sinusoidal pattern about the periphery of the container, thereby generating a cylindrical lens along optical path 44. Note that the contact angles may not be perfectly sinusoidal when the lens is cylindrical in light of effects of the normals to the cylinder wall, the use of discrete, electrodes, etc. The cylindrical power of the lens may be changed by changing a cylindrical power voltage $V_c$ of source 88, thereby changing the amplitude of the sinusoidal voltage pattern.

Figure 7B:

Referring now to FIGS. 5, 7A, and 7B, a spherical power component can be introduced into fluid/fluid interface 66 by changing the voltage pattern so that an average voltage of the pattern is more positive or more negative. In other words, by shifting the voltage pattern upward relative to a purely cylindrical voltage pattern, such as by increasing a spherical voltage component $V_s$, the average contact angle of the fluid/fluid interface 66 along the circumferential wall of container 82 may be driven to produce and/or superimpose a spherical bulge within the fluid lens.

Figure 6:
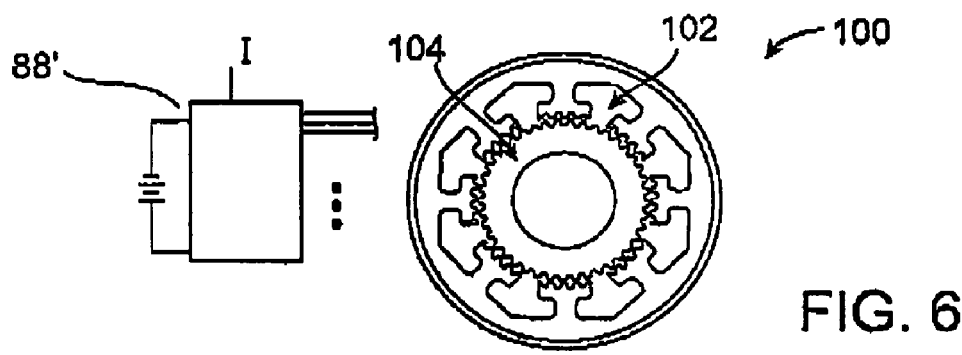
FIG. 6 schematically illustrates components of a stepper motor which may be modified for use with the variable fluid lens apparatus of FIG. 5.

Referring now to FIGS. 5-7B, shifting of a cylindrical orientation 92 may be effected in a relatively simple mode by shifting the voltage pattern circumferentially one full electrode, for example, in the positive $\theta$ direction. This allows a series of discrete cylindrical axes 92 to be provided with a relatively simple source 88, with switching of the pattern occurring in response to an input I. More sophisticated cylindrical orientation shifting techniques may be borrowed from technology developed for microstepping of electrical step hybrid motors 100, as seen in FIG. 6. A microstepping controller 88 applies a pattern of currents to the teeth of a stator 102 so as to drive a rotor 104 to a desired position. In standard stepping mode, source 88 may apply a voltage pattern to stator 102, and may shift that current pattern discretely from one tooth to the next so as to effect one full rotational step of rotor 104. Where a relatively large number of stator teeth are provided, such as in standard 200 step motors, this provides a relatively fine rotational pattern. However, even finer rotational capabilities may be provided by gradually shifting the currents about the individual teeth of the stator, so that the current pattern shifts rotationally less than one full tooth at a time. Such microstepping techniques allow commercially available stepper motors to separate a single step into a as many as 500 microsteps, giving 100,000 or more steps per full revolution of the rotor 104.

A driver 88' coupled to stepper motor 100 may be modified for use in the flexible fluid lens 80 of FIG. 5, for example, by attaching resistors to the current outputs of rotor drivers so as to provide a voltage pattern rather than a current pattern. Alternatively, the techniques developed for microstepper motors may be used to develop a new "microstepping" fluid lens drive circuit. Regardless, application of such microstepping pattern-shifting techniques may allow cylindrical orientation 92 of fluid lens 80 to be driven to more rotational orientations than there are individual electrodes 86 in the circumferential array.

While the exemplary embodiments have been described in detail for clarity of understanding and by way of example, a variety of adaptations, changes, and modifications will be obvious to those of skill in the art. For example, while the inputs into the optical assembly of FIG. 1 are schematically illustrated as mechanical knobs, the input may actually be provided by digital signals electrically or optically transmitted to processor 30 of source 22. Furthermore, while the fluid lens assembly 20 of apparatus 12 in FIG. 1 is shown for use as a phoropter, the structure may be readily adapted for use in an automatic refractor, or the like. Additionally, along with cylindrical and spherical lenses, the fluid lenses of the present invention may be used to provide other anamorphic lens shapes, including those described in U.S. Pat. No. 3,751,138. Hence, the scope of the present invention is limited solely by the appended claims.

What is claimed is:

1. An optical apparatus comprising:
    at least one housing defining a first opening, a second opening, and a third opening having an optical path therethrough, the openings each comprising a rectangular cross-section;
    a plurality of fluids disposed in the openings so as to define a first fluid/fluid interface in the first opening, a second fluid/fluid interface in the second opening, and a third fluid/fluid interface in the third opening; and
    an electrical potential source coupled to the at least one opening so as to apply a plurality of electrowetting potentials, the source configured to vary at least one of the electrowetting potentials in response to a first input so that the one or more fluid/fluid interfaces change at least a cylindrical orientation of the optical path;
    wherein varying a first electrowetting potential effects changes in a first variable cylindrical power of the first fluid interface, the first variable cylindrical power having a first cylindrical orientation extending laterally across the optical path, varying a second electrowetting potential effects changes in a second variable cylindrical power of the second fluid interface, the second variable cylindrical power having a second cylindrical orientation extending laterally across the optical path, and varying a third electrowetting potential effects changes in a third variable cylindrical power of a third fluid/fluid interface disposed within the third opening, the third variable cylindrical power having a third cylindrical orientation extending laterally across the optical path, the first cylindrical orientation being angularly offset from the second cylindrical orientation about the optical path, the third cylindrical orientation being angularly offset from the first and second cylindrical orientations about the optical path.

2. The apparatus of claim 1, wherein the source is configured to alter the at least one electrowetting potentials in response to a second input so that the one or more fluid/fluid interfaces vary a spherical power in response to a second input, and so that the one or more fluid/fluid interfaces vary a cylindrical power in response to a third input, the one or more fluid/fluid interfaces having a sphero-cylindrical power along the optical path.

3. The apparatus of claim 1, wherein the first cylindrical orientation is substantially perpendicular to the second cylindrical orientation, and wherein the third cylindrical orientation is angularly offset from the first cylindrical orientation by about 45 degrees.

4. The apparatus of claim 1, further comprising first and second electrodes along opposing sides of the first opening, and third and forth electrodes along opposing sides of the second opening.

5. The apparatus of claim 1, wherein the housing comprises a wall disposed around the optical path, and further comprising a plurality of conductors distributed circumferentially about the wall.

6. The apparatus of claim 5, wherein the conductors define an electrode array with each electrode of the array disposed circumferentially between and electrically separated from two adjacent electrodes of the array.

7. The apparatus of claim 5, wherein the power source applies a circumferential series of potentials about the optical path.

8. The apparatus of claim 1, wherein the optical apparatus varies a cylindrical power in response to a second input and the cylindrical orientation in response to the first input by effecting movement of the fluids within the at least one housing and without effecting other movement of the apparatus.

9. The apparatus of claim 8, wherein the apparatus can vary the cylindrical power throughout a range from at least −20.0 diopters to at least about +20.0 diopters, wherein the apparatus can vary the cylindrical orientation throughout about 180 degrees, and wherein the apparatus can vary a spherical power throughout a range from at least −6.0 to at least +6.0.

10. The apparatus of claim 8, wherein the power source comprises a processor, the processor determining the plurality of electrowetting potentials in response to the first and second inputs.

11. The apparatus of claim 10, wherein the processor further determines the electrowetting potentials in response to a third input so as to vary a spherical optical power along the optical path.

12. The apparatus of claim 1, wherein the plurality of electrical conductors comprise first and second electrodes along opposing sides of the first opening, and third and forth electrodes along opposing sides of the second opening.

13. A fluid cylindrical lens apparatus comprising:
    a first housing having a first prismatic opening with an optical path therethrough, the first opening having a first surface and a second surface, the second surface offset from the first surface with the optical path extending between and offset from the first surface and the second surface;
    a plurality of fluids disposed in the opening so as to define a first fluid/fluid interface extending from the first surface to the second surface across the optical path;
    an electrical potential source coupled to the first and second surfaces to apply a first variable potential thereto so as to change a first variable cylindrical power of the fluid/fluid interface along the optical path.

14. The fluid cylindrical lens apparatus of claim 13, wherein the first variable cylindrical power has a first orientation traversing end surfaces of the first opening, wherein the electrical potential source applies another potential to the end surfaces, the other potential being different than the first potential, and further comprising:
    a second housing having a second opening, the second opening having a third surface and a forth surface with the optical path therebetween;
    a plurality of fluids disposed in the second opening so as to define a second fluid/fluid interface therebetween;
    the power source coupled to the third and fourth surfaces to apply a second variable potential thereto so as to change a second variable cylindrical power having a second orientation, the second orientation angularly offset about the optical path relative to the first orientation;
    a third housing having a third opening, the third opening having a fifth surface and a sixth surface with the optical path therebetween;

a plurality of fluids disposed in the third opening so as to define a third fluid/fluid interface therebetween;

the potential source coupled to the fifth and sixth surfaces to apply a third variable potential thereto so as to change a third cylindrical power having a third orientation, the third orientation angularly offset from the first and second axes so as to allow the fluid cylindrical lens apparatus to vary spherical power along the optical path, cylindrical power along the optical path, and cylindrical orientation along the optical path.

* * * * *